United States Patent [19]

Tatsuoka et al.

[11] Patent Number: 4,889,853
[45] Date of Patent: Dec. 26, 1989

[54] HYDROQUINONLYPHENYL BUTYRIC ACID AMIDE DERIVATIVE

[75] Inventors: Toshio Tatsuoka, Nishinomiya; Kenji Suzuki, Osaka; Fumio Satoh, Nagaoka; Seiji Miyano, Fukuoka; Kunihiro Sumoto, Ohnojo, all of Japan

[73] Assignee: Suntory Limited, Osaka, Japan

[21] Appl. No.: 216,337

[22] Filed: Jul. 8, 1988

[30] Foreign Application Priority Data

Jul. 9, 1987 [JP] Japan .................. 62-169683

[51] Int. Cl.⁴ .................. A61K 31/535; A61K 31/54; C07D 265/30; C07D 279/12
[52] U.S. Cl. .............. 514/227.5; 514/227.8; 514/237.5; 544/58.4; 544/171
[58] Field of Search ............ 544/58.4, 171; 514/227.5, 227.8, 237.5

[56] References Cited

FOREIGN PATENT DOCUMENTS 61-44840  3/1986  Japan .
62-226953 10/1987  Japan .

*Primary Examiner*—Richard L. Raymond
*Attorney, Agent, or Firm*—Burns, Doane, Swecker & Mathis

[57] ABSTRACT

A hydroquinonylphenyl butyric acid amide derivative having the formula (I):

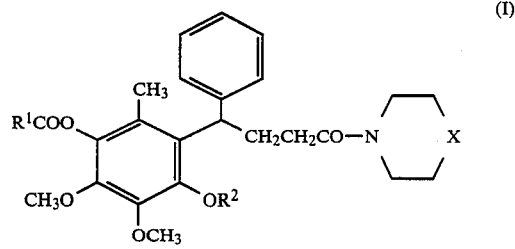

wherein $R^1$ represents an aromatic or heterocyclic group which may be substituted, $R^2$ represents a hydrogen atom, a lower alkylcarbonyl group, an aromatic carbonyl or heterocyclic carbonyl group which may be substituted, and X represents an oxygen atom or sulfur atom or a pharmaceutically acceptable salt thereof, which has a cerebral insufficiency improving activity.

6 Claims, No Drawings

HYDROQUINONLYPHENYL BUTYRIC ACID AMIDE DERIVATIVE

BACKGROUND OF THE INVENTION

1. Field of the Invention

The present invention relates to novel hydroquinonylphenyl butyric acid amide derivatives and pharmaceutically acceptable salts thereof and pharmaceutical compositions having a cerebral insufficiency improving activity containing the same as an active ingredient.

These compounds can be widely utilized because they are effective for ameliorating and curing various symptoms based on cerebral organic disorders and pathergasia.

The term "cerebral organic disorders" used herein means various symptoms derived from cerebral ischemic diseases such as cerebral infarct sequela, cerebral hemorrhage sequela, and cerebral arteriosclerosis sequela and various organic disorders derived from senile dementia, dementia presenilis, amnesia, cephalic traumatic sequela, and cerebral operation sequela. Furthermore, the term pathergasia used herein means psychogender organic diseases derived from mania, melancholia, neurosis, Parkinson's disease, schizophrenia, schizophrenia-like disorders, and chorea (Huntington's chorea) as well as medicines and alcoholic beverages.

2. Description of the Related Art

Cerebral cells retain their own intracellular environments which are completely different from the surrounding environments, i.e., extracellular fluids, and while this difference is maintained, the cerebral cells are alive. Accordingly, energy must be always generated and supplied to cerebral cells, and most of the energy required by cerebral nerve cells is supplied by oxygen and glucose. These energy sources are not substantially stored in the brain, however, and therefore, are always supplied from the blood.

If certain cerebral disturbances or disorders occur, and if the supply of oxygen and glucose to the brain is stopped, generally a gradual or stepwise degression in energy metabolism occurs, and as a result, the functions of the cells are lost with the elapse of time and the cells are soon organically disrupted, and, thus the normal functions of the cerebral cells cannot be effected. Therefore, a mechanism for adjusting cerebral bloodstreams in the cerebral blood vessels, per se, has been fully developed to ensure a stable supply of these energy sources to the cerebral tissues and to maintain the outer environments of the cerebral nerve cells.

Various cerebral circulating improvers, cerebral vasodilators, and cerebral excitometabolites have been heretofore used for the medical treatment of cerebral blood vessel disorders, but although these medicines are effective for ameliorating subjective symptoms, no substantial amelioration of neural symptoms and mental symptoms thereby has been observed.

In this connection, Japanese Unexamined Patent Publication (Kokai) No. 61-44840 discloses various derivatives of benzoquinonyl alkanoic acids, which are described as effective as an antiasthmatic agent, an antiallergic agent or a cerebral circulating improver.

SUMMARY OF THE INVENTION

An object of the present invention is to provide a novel compound having effective activities for ameliorating and curing (or treating) cerebral organic disorders, by oral administration.

Other objects and advantages of the present invention will be apparent from the following description.

In accordance with the present invention, there is provided a hydroquinonylphenyl butyric acid amide derivative having the formula (I):

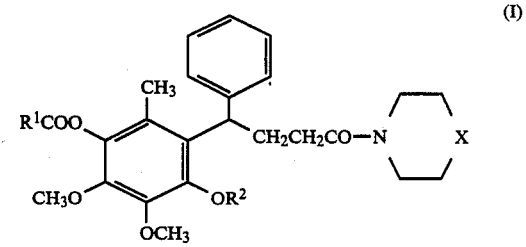

wherein $R^1$ represents an aromatic or heterocyclic group which may be substituted, $R^2$ represents hydrogen atom, a lower alkylcarbonyl group, an aromatic carbonyl or heterocyclic carbonyl group which may be substituted, and X represents oxygen atom or sulfur atom.

In accordance with the present invention, there is also provided a pharmaceutical composition having a cerebral insufficiency improving activity comprising, as an active ingredient, a pharmaceutical effective amount of a hydroquinonylphenyl butyric acid amide derivative having the above-mentioned formula (I) or a pharmaceutically acceptable salt thereof.

DESCRIPTION OF THE PREFERRED EMBODIMENTS

The present inventors have found that various derivatives of hydroxyphenyl butyric acid amide having the above-mentioned formula (I) are extremely effective against cerebral anoxia of test animals, at a low dosage, and therefore, are an effective improver of, or remedy for, cerebral organic disorders.

In the above-mentioned formula (I) according to the present invention, the aromatic group $R^1$ may include, for example, aryl groups such as phenyl and naphthyl, and the heterocyclic group may include, for example, pyridyl groups (e.g., 2-pyridyl, 3-pyridyl, 4-pyridyl), dihydropyridyl groups, N-methylhydropyridyl groups, thienyl groups, furyl groups, and these groups may be substituted with, for example, a hydroxyl group, alkoxy group, alkyl group, halogen atom.

The lower alkylcarbonyl group $R^2$ may include, for example, lower alkanoic acid acyl groups such as acetyl, propionyl, and butyryl groups and the aromatic carbonyl groups may include, for example, a benzoyl group and naphthoyl groups, the heterocyclic carbonyl groups may include, for example, furolyl, thenoyl, nicotinoyl, isonicotinoyl, pyridine-2-carbonyl, and dihydropyridinecarbonyl groups, and all of these may be also substituted with, for example, an alkyl group, hydroxyl group, alkoxy group, and halogen atom.

The compounds according to the present invention having the above-mentioned formula (I) can be synthesized, for example, as described below.

Namely, 8,9-dimethoxy-7-hydroxy-6-methyl-5-phenyl-2-oxo-2,3,4,5-tetrahydrobenzoxepin obtained by the reaction between the known compounds —phenyl—-butyrolactone and 2,3-dimethoxy-5-methyl-1,4-hydroquinone in the presence of an acid such as polyphosphoric acid or sulfuric acid is reacted with a carboxylic acid having the formula (II):

$$R^1COOH \quad (II)$$

wherein $R^1$ is as defined above or an acid anhydride or acid halide thereof, according to any conventional esterification method, a benzoxepin derivative having the formula (III):

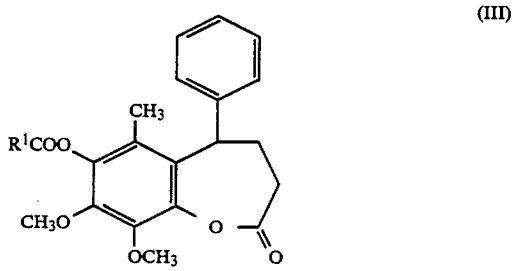

wherein $R^1$ is as defined above can be obtained.

The compound (III) obtained above and morpholine or thiomorpholine can be reacted by heating in an inert solvent such as benzene or toluene, or the product is further allowed to react with a carboxylic acid having the formula (IV):

$$R^3COOH \quad (IV)$$

wherein $R^3$ represents a lower alkyl group, aromatic group or heterocyclic group, which may be substituted or an acid anhydride or acid halide thereof, to give the hydroquinonylphenyl butyric acid amide derivative of the present invention having the formula (I).

As mentioned above, the derivatives of hydroquinonylphenyl butyric acid amide having the formula (I) according to the present invention are effective for ameliorating and curing various symptoms based on cerebral organic disorders. This is clear from the later described Evaluation Examples showing that the present compounds (I) have an excellent antihypoxia activity against test animals.

When the present derivatives are used as a medicine, there are no critical limitations to the administration methods thereof.

The compounds having the general formula (I) according to the present invention can be administered alone or in combination with pharmaceutically acceptable conventional carriers, excipients, and fillers in a variety of dosage forms such as tablets, troches, pills, granules, powders, capsules, ampules, suppositories and the like. The excipients include, for example, starch, dextrin, sucrose, lactose, silic acid, carboxymethylcellulose, cellulose, gelatin, polyvinylpyrrolidone, glycerin, agar, calcium carbonate, sodium dicarbonate, paraffin, cetyl alcohol, stearic acid esters, kaolin, bentonite, talc, calcium stearate, magnesium stearate, polyethyleneglycol, water, ethanol, isopropyl alcohol and propyleneglycol. The present compounds may be, for example, parenterally administered, in the form of, for example, injections or suppositories.

Although there are no critical limitations to the dosage range of the present cerebral insufficiency improver, the optimum dosage range of the compound (I) of the present invention is 0.1 to 1000 mg, preferably 10 to 500 mg, per day. This dosage range can be suitably changed depending upon, for example, the characteristics of the subjects, including age, response, weight, severity of disease and the like, the administration methods, the dosage forms, and the dosing frequency.

EXAMPLES

The present invention now will be further illustrated by, but is by no means limited to, the following Synthesis Examples, Formulation Examples, and Evaluation Examples.

Example 1 (Compound No. 1)

4-(3,4-Dimethoxy-2-hydroxy-6-methyl-5-nicotinoyloxy)phenyl-4-phenyl-1-thiomorpholino-1-oxobutane A 340 mg (0.785 mmole) amount of 8,9-dimethoxy-6-methyl-7-nicotinoyloxy-5-phenyl-2-oxo-2,3,4,5-tetrahydro-1-benzoxepin obtained in Reference Example 2 as described below was dissolved in 20 ml of toluene, and 89 mg (0.864 mmole) of thiomorpholine was added to the solution, followed by stirring at 100° C. for 1 hour. The reaction mixture was concentrated under a reduced pressure and the residue was subjected to silica gel chromatography (hexane:ethyl acetate-1:2) to obtain 352 mg of the title compound (84%).

Examples 2 to 4

The compounds of Examples 2 to 4 were obtained by using corresponding compounds obtained in Reference Examples 3, 4 and 5 as described below instead of 8,9-dimethoxy-6-methyl-7-nicotinoyloxy-5-phenyl-2-oxo-2,3,4,5-tetrahydro-1-benzoxepin.

Example 2 (Compound No. 2)

4-(3,4-Dimethoxy-2-hydroxy-5-isonicotinoyloxy-6-methyl)phenyl-4-phenyl-1-thiomorpholino-1-oxobutane
Yield: 66%

Example 3 Compound No. 3)

4-(3,4-Dimethoxy-2-hydroxy-6-methyl-5-picolinoyloxy)-phenyl-4-phenyl-1-thiomorpholino-1-oxobutane
Yield: 83%

Example 4 (Compound No. 4)

4-(5-Benzoyloxy-3,4-dimethoxy-2-hydroxy-6-methyl)-phenyl-4-phenyl-1-thiomorpholino-1-oxobutane
Yield: 94%

Example 5 (Compound No. 5)

4-(3,4-Dimethoxy-2-hydroxy-6-methyl-5-nicotinoyloxy)phenyl-4-phenyl-1-morpholino-1-oxobutane A 297 mg (0.686 mmole) amount of 8,9-dimethoxy-6-methyl-7-nicotinoyloxy-5-phenyl-2-oxo-2,3,4,5-tetrahydro-1-benzoxepin was dissolved in 20 ml of toluene, and 66 mg (0.759 mmole) of morpholine was added to the solution followed by stirring at 100° C. for one hour. The reaction mixture was then treated in the same manner as in Example 1 to give 276 mg (77%) of the desired product.

Examples 6 to 8

The compounds of Examples 6 to 8 were obtained by the same reaction as caused in Example 5 by using corresponding compounds respectively in Reference Examples 3, 4, and 5 as described below instead of 8,9-dimethoxy-6-methyl-7-nicotinoyloxy-5-phenyl-2-oxo-2,3,4,5-tetrahydro-1-benzoxepin.

Example 6 (Compound No. 6)

4-(3,4-Dimethoxy-2-hydroxy-5-isonicotinoyloxy-6-methyl)phenyl-4-phenyl-1-morpholino-1-oxobutane
Yield: 75%

Example 7 (Compound No. 7)

4-(3,4-Dimethoxy-2-hydroxy-6-methyl-5-picolinoyloxy)phenyl-4-phenyl-1-morpholino-1-oxobutane
Yield 75%

Example 8 (Compound No. 8)

4-(5-Benzoyloxy-3,4-dimethoxy-2-hydroxy-6-methyl)-phenyl-4-phenyl-1-morpholino-1-oxobutane
Yield: 75%

Example 9 (Compound No. 9)

4-(2,5-Dibenzoyloxy-3,4-dimethoxy-6-methyl)phenyl-4-phenyl-1-thiomorpholino-1-oxobutane A 113 mg (0.211 mmole) amount of 4-(5-benzoyloxy-3,4-dimethoxy-2-hydroxy-6-methyl)phenyl-4-phenyl-1-thiomorpholino-1-oxobutane obtained in Example 1 was dissolved in 10 ml of methylene chloride, and 39 mg (0.211 mmole) of benzoic acid, 61 mg (0.318 mmole) of 1-ethyl-3-(3-dimethylaminopropyl)-carbodiimide hydrochloride and 3 mg of 4-dimethylaminopyridine were added, followed by stirring at room temperature for 5 hours. The reaction mixture was treated in the same manner as in Example 1 to give 112 mg (83%) of the title compound.

Example 10 (Compound No. 10)

4-(2,5-Dibenzoyloxy-3,4-dimethoxy-6-methyl)phenyl-4-phenyl-1-morpholino-1-oxobutane In Example 9, instead of 4-(5-benzoyloxy-3,4-dimethoxy-2-hydroxy-6-methyl)phenyl-4-phenyl-1-thiomorpholino-1-oxobutane, 4-(5-benzoyloxy-3,4-dimethoxy-2-hydroxy-6-methyl)phenyl-4-phenyl-1-morpholino-1-oxobutane was used, followed by the same treatment as in Example 1 to obtain 143 mg (73%) of the title compound.

Example 11 (Compound No. 11)

4-(2-Acetoxy-5-benzoyloxy-3,4-dimethoxy-6-methyl)-phenyl-4-phenyl-1-thiomorpholino-1-oxobutane A 248 mg (0.464 mmole) amount of 4-(5-benzoyloxy-3,4-dimethoxy-2-hydroxy-6-methyl)phenyl-4-phenyl-1-thiomorpholino-1-oxobutane was dissolved in 5 ml of acetic anhydride, 5 ml of pyridine and 5 mg of 4-dimethylaminopyridine, and the solution was stirred at room temperature for 5 hours. The reaction mixture was treated in the same manner as in Example 1 to obtain 232 mg (87%) of the desired compound.

Example 12 (Compound No. 12)

4-(2-Acetoxy-5-benzoyloxy-3,4-dimethoxy-6-methyl)-phenyl-4-phenyl-1-morpholino-1-oxobutane By using 283 mg (0.545 mmol) of 4-(5-benzoyloxy-3,4-dimethoxy-2-hydroxy-6-methyl)phenyl-4-phenyl-1-morpholino-1-oxobutane in Example 5, and treating the product in the same manner as in Example 11, 280 mg (92%) of the desired compound was obtained.

Examples 13 to 17 (Compounds No. 13 to 17)

By use of the compounds of Examples 1, 2 and 5, and the products were treated in the same manner as in Example 9 or Example 11 to synthesize the compounds of the Compounds No. 13 to 17.

The physicochemical properties of the compounds obtained in the above-mentioned Examples 1 to 17 are shown in Table 1.

TABLE 1

Structure:

R¹COO, Me, MeO, OMe, OR², phenyl, CH₂CH₂CO—N(X) (piperidine/morpholine ring with X)

| Compound No. | R¹ | R² | X | Property (mp) | IR spectrum (ν cm⁻¹) | NMR spectrum (δ ppm) | Mass spectrum | Elemental analysis |
|---|---|---|---|---|---|---|---|---|
| 1 | 3-pyridyl | H | S | 144–145° C. | 1632 1738 | 2.02(3H,s) 2.30(2H,t) 2.4–2.75(6H,m) 3.5–3.7(2H,m) 3.7–4.0(2H,m) 3.82(3H,s) 3.93(3H,s) 4.4–4.0(2H,m) 4.4–4.0(1H,m) 7.1–7.4(5H,m) 7.4–7.55(5H,m) 8.35–8.55 (1H,m) 8.8–8.9(1H,m) 9.4(1H,s-like) | 536 (M⁺) 392 (100) | Anal Calcd for C:64.90 H:6.01 N:5.22 Found C:64.78 H:5.92 N:5.24 |
| 2 | 4-pyridyl | H | S | 100–102° C. | 1628 1750 | 2.00(3H,s) 2.29(2H,t) 2.4–2.75(6H,m) 3.5–3.7(2H,m) 3.7–4.0(2H,m) 3.81(3H,s) 3.93(3H,s) 4.45–4.6(1H,m) 7.1–7.4(5H,m) 7.9–8.1(2H,m) 8.8–8.9(2H,m) | 536 (M⁺) 268 (100) High Mass Calcd. 536.1979 Found. 536.2004 | — |
| 3 | 2-methylpyridyl | H | S | 101–103° C. | 1628 1736 | 2.03(3H,s) 2.28(2H,t) 2.4–2.75(6H,m) 3.7–4.0(2H,m) 3.86(3H,s) 3.93(3H,s) 4.4–4.65(1H,m) 7.45–7.65(1H,m) 7.05–7.4(5H,m) 7.8–8.0(1H,m) 8.27(1H,d) 8.83(1H,d) | 536 (M⁺) 392 (100) High Mass Calcd. 536.1979 Found. 536.2026 | — |
| 4 | phenyl | H | S | 102–104° C. | 1628 1734 | 2.01(3H,s) 2.30(2H,t) 2.4–2.75(6H,m) 3.5–3.7(2H,m) 3.7–4.0(2H,m) 3.82(3H,s) 3.95(3H,s) 3.4–3.65(5H,m) 7.05–7.4(5H,m) 7.52(2H,t) 7.66(1H,t) 8.20(2H,d) | 535 (M⁺) 105 (100) | Anal Calcd for C:67.27 H:6.21 N:2.62 Found C:67.06 H:6.27 N:2.58 |
| 5 | 3-pyridyl | H | O | 71–73° C. | 1628 1737 | 2.02(3H,s) 2.30(2H,t) 2.45–2.8(2H,m) 3.2–3.45(2H,m) 3.45–3.75(6H,m) 3.82(3H,s) 3.93(3H,s) 4.4–4.6(1H,m) 7.05–7.4(5H,m) 7.4–7.55(5H,m) 8.44(1H,d) 8.86(1H,d) 9.40(1H,s) | 520 (M⁺) 392 (100) High Mass Calcd. 520.2207 Found. 520.2223 | — |

TABLE 1-continued

| Compound No. | R¹ | R² | X | Property (mp) | IR spectrum ($\nu$ cm$^{-1}$) | NMR spectrum ($\delta$ ppm) | Mass spectrum | Elemental analysis |
|---|---|---|---|---|---|---|---|---|
| 6 | 4-pyridyl | H | O | 79–82° C. | 1628, 1742 | 2.01(3H,s) 2.2–2.4(2H,m) 2.45–2.75(2H,m) 3.25–3.4(2H,m) 3.45–3.7(6H,m) 3.82(3H,s) 3.94(3H,s) 4.4–4.6(1H,m) 7.1–7.4(5H,m) 7.99(2H,d) 8.87(2H,d) | 520 (M⁺) 268 (100) High Mass Calcd. 520.2206 Found. 520.2192 | — |
| 7 | 2-methylpyridyl | H | O | 97–98° C. | 1628, 1736 | 2.05(3H,s) 2.29(2H,t) 2.5–2.7(2H,m) 3.2–3.4(2H,m) 3.45–3.75(6H,m) 3.84(3H,s) 3.93(3H,s) 4.45–4.6(1H,m) 7.1–7.4(5H,m) 7.45–7.6(1H,m) 7.8–8.0(1H,m) 8.27(1H,d) 8.84(1H,d) | 520 (M⁺) 129 (100) High Mass Calcd. 520.2207 Found. 520.2179 | — |
| 8 | phenyl | | O | 101–102° C. | 1628, 1734 | 2.02(3H,s) 2.30(2H,t) 2.4–2.8(2H,m) 3.2–3.45(2H,m) 3.45–3.7(6H,m) 3.82(3H,s) 3.93(3H,s) 4.4–4.6(1H,m) 7.05–7.4(5H,m) 7.51(2H,t) 7.64(1H,t) 8.20(2H,d) | 519 (M⁺) 105 (100) | Anal Calcd for C:69.35 H:6.39 O:270 Found C:69.36 H:6.39 O:2.66 |
| 9 | phenyl | PhC(=O) | S | Colorless powder (74–76° C.) | 1628, 1736 | 2.03(3H,br s) 2.1–2.8(8H,m) 3.5–3.75(2H,m) 3.75–4.00(2H,m) 3.82(3H,s) 3.87(3H,s) 4.45–4.70(1H,m) 7.0–8.3(15H,m) | — | — |
| 10 | phenyl | PhC(=O) | O | Colorless powder (80–82° C.) | 1638, 1734 | 2.06(3H,br s) 2.1–2.8(4H,m) 3.25–3.45(2H,m) 3.45–3.75(6H,m) 3.82(3H,s) 3.86(3H,s) 4.5–4.65(1H,m) 7.0–8.3(15H,m) | — | — |

General structure:

R'COO—[aryl with Me, OR², OMe, MeO substituents]—CH(Ph)—C(=O)—N(morpholine ring with X)

TABLE 1-continued

| Compound No. | R¹ | R² | X | Property (mp) | IR spectrum ($\nu$ cm$^{-1}$) | NMR spectrum ($\delta$ ppm) | Mass spectrum | Elemental analysis |
|---|---|---|---|---|---|---|---|---|
| 11 | 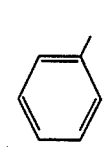 | CH₃CO— | S | Colorless powder (71–73° C.) | 1636 1738 1760 | 2.01(3H.br s) 2.10(3H.br s) 2.1–2.8(8H.m) 3.5–3.7(2H.m) 3.75–3.95(2H.m) 3.83(3H.s) 3.85(3H.s) 4.4–4.6(1H.m) 7.1–7.35(5H.m) 7.4–7.75(3H.m) 8.11(2H.d) | — | — |
| 12 | 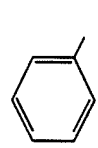 | CH₃CO— | O | Colorless powder (67–69° C.) | 1632 1738 1760 | 2.02(3H.br s) 2.10(3H.br s) 2.1–2.8(4H.m) 3.25–3.4(2H.m) 3.5–3.85(6H.m) 3.82(3H.s) 3.83(3H.s) 4.4–4.6(1H.m) 7.1–7.35(5H.m) 7.45–7.75(3H.m) 8.22(2H.d) | — | — |
| 13 | 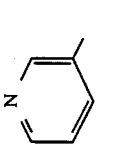 | 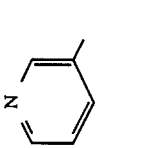 | S | Colorless powder (75–77° C.) | 1640 1746 | 2.0–2.8(1H.m) 3.5–3.7(2H.m) 3.7–4.0 (2H.m) 3.81(3H.s) 3.85(3H.s) 4.45–4.7 (1H.m) 6.95–7.35(5H.m)7.35–7.6(2H.m) 8.1–8.4(1H.m) 8.49(1H.d) 8.83(1H.d) 8.90(1H.d) 9.17(1H.br s) 9.44(1H.s) | 641 (M⁺) 106 (100) High Mass Calcd. 641.2193 Found. 641.2166 | — |
| 14 | 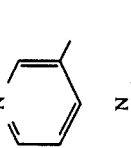 | 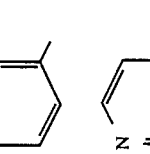 | O | Colorless powder (79–81° C.) | 1636 1744 | 2.13(3H.br s) 2.1–2.8(4H.m) 3.25–3.45 (2H.m) 3.45–3.7(6H.m) 3.81(3H.s) 3.86 (3H.s) 4.45–4.7(1H.m) 6.9–7.4(5H.m) 7.41(1H.dd) 7.52(1H.dd) 8.05–8.3(1H.m) 8.4–8.55(1H.m) 8.85–8.95(2H.m) 9.17 (1H.br s) 9.44(1H.s) | — | — |
| 15 | 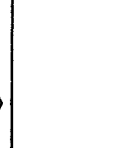 | CH₃CO— | S | Colorless powder (65–68° C.) | 1638 1744 1760 | 2.03(3H.br s) 2.11(3H.br s) 2.1–2.45 (3H.m) 2.45–2.8(5H.m) 3.5–3.7(2H.m) 3.7–4.0(2H.m) 3.84(6H.s) 4.4–4.6(1H.m) 7.1–7.4(5H.m) 7.49(1H.dd) 8.46(1H.d) 8.87(1H.d) 9.42(1H.s) | 578 (M⁺) 106 (100) High Mass Calcd. 578.2085 Found. 578.2110 | — |
| 16 |  | CH₃CO— | O | Colorless powder (64–66° C.) | 1638 1744 1760 | 2.01(3H.br s) 2.12(3H.br s) 2.1–2.8 (4H.m) 3.2–3.4(2H.m)3.45–3.75(6H.m) 3.82(6H.s) 4.4–4.6(1H.dd) 7.1–7.35 (5H.m) 7.49(1H.dd) 8.46(1H.d) 8.88(1H.d) 9.40(1H.s) | — | — |
| 17 |  | CH₃CO— | S | Colorless powder (74–76° C.) | 1640 1742 | 2.01(3H.br s) 2.12(3H.br s) 2.1–2.8(8H.m) 3.5–3.7(2H.m) 3.81(3H.s) 3.83(3H.s) 3.75–3.95(2H.m) 3.4–3.6(1H.m) 7.1–7.35(5H.m) 7.99(2H.d) 8.88(2H.d) | — | — |

Reference Example 1

8,9-Dimethoxy-7-hydroxy-6-methyl-5-phenyl-2-oxo-2,3,4,5-tetrahydrobenzoxepin

An amount of 18.4 g of 2,3-dimethoxy-5-methylhydroquinone and 16.2 g of γ-phenyl-γ-butyrolactone was stirred in 150 ml of polyphosphoric acid at room temperature for 5 hours. The reaction mixture obtained was poured into ice-water and extracted with ether, and the ether extract was washed with water and then dried over magnesium sulfate and concentrated. The concentrated residue was purified by silica gel column chromatography/hexane:ethyl acetate (2:1), and thus 6.10 g (18.6%) of the desired compound was obtained.

Reference Example 2

8,9-Dimethoxy-6-methyl-7-nicotinoyloxy-5-phenyl-2-oxo-2,3,4,5-tetrahydro-1-benzoxepin

To a solution of 700 mg (2.124 mmole) of 700 mg of 8,9-dimethoxy-7-hydroxy-6-methyl-2-oxo-2,3,4,5-tetrahydro-1-benzoxepin dissolved in 50 ml of methylene chloride, 342 mg (2.778 mmole) of niconitic acid, 614 mg (3.203 mmole) of 1-ethyl-3-(3-dimethylaminopropyl)carbodiimide hydrochloride and 10 mg of 4-dimethylaminopyridine were added, and the mixture was stirred at room temperature for 5 hours. The reaction mixture was washed with water, then dried over magnesium sulfate and filtered, followed by evaporation of the solvent. The residue was subjected to silica gel column chromatography (hexane:ethyl acetate=2:3) to obtain 738 mg (80%) of the desired compound. The physicochemical properties are shown in Table 2.

Reference Examples 3 to 5

In Reference Example 1, isonicotinic acid, picolic acid and benzoic acid were used instead of nicotinic acid, and the reaction was carried out similarly to obtain the compounds of Reference Examples 3 to 5. The physicochemical properties of the compounds obtained are shown in Table 2.

Reference Example 3

8,9-Dimethoxy-7-isonicotinoyloxy-6-methyl-5-phenyl-2-oxo-2,3,4,5-tetrahydro-1-benzoxepin

Yield: 76%

Reference Example 4

8,9-Dimethoxy-6-methyl-7-nicotinoyloxy-5-phenyl-2-oxo-2,3,4,5-tetrahydro-1-benzoxepin

Yield: 43%

Reference Example 5

7-Benzoyloxy-8,9-dimethoxy-6-methyl-5-phenyl-2-oxo-2,3,4,5-tetrahydro-1-benzoxepin

Yield: 74%

TABLE 2

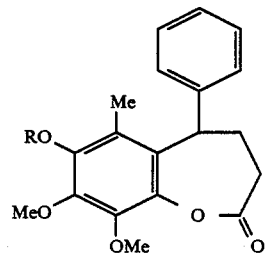

| Reference Example No. | R | Yield (%) | Property (mp) | IR spectrum ($\nu$ cm$^{-1}$) | NMR spectrum ($\delta$ ppm) | Mass spectrum | Elemental analysis |
| --- | --- | --- | --- | --- | --- | --- | --- |
| 1 | H | 16.8 | Oily substance | 3500 1752 | 2.21(3H.s) 2.30–2.70(3H.m) 2.80–3.00 (1H.m) 3.83(3H.s) 3.99(3H.s) 4.55–4.70 (1H.m) 5.86(1H.s) 7.10–7.35(5H.m) 3.5–4.0(1H.m) | $C_{19}H_{20}O_5$ Mass 328 (M$^+$) 211 (100) | — |
| 2 | 3-pyridyl-CO— | 80 | Colorless powder (166–168° C.) | 1752 | 2.15(3H.s)2.3–2.8(3H.m) 2.8–3.0(1H.m) 3.87(3H.s) 3.90(3H.s) 4.55–4.75(1H.m) 7.05–7.40(5H.m) 7.4–7.6(1H.m) 8.4–8.55(1H.m) 8.8–8.95(1H.m) 9.46(1H.s-like) | 433 (M$^+$.100) | Anal Calcd for C:69.27 H:5.35 N:3.23 Found C:69.12 H:5.34 N:3.15 |
| 3 | 4-pyridyl-CO— | 76 | Colorless powder (151–152° C.) | 1754 | 2.12(3H.s) 2.3–2.8(3H.m) 2.8–3.0(1H.m) 3.86(3H.s) 3.89(3H.s) 4.55–4.7(1H.m) 7.1–7.4(5H.m) 8.03(2H.d) 8.89(2H.d) | 433 (M$^+$) 378 (100) | Anal Calcd for C:69.27 H:5.35 N:3.23 Found C:69.34 H:5.40 N:3.17 |
| 4 | 2-pyridyl-CO— | 43 | Colorless powder (70–72° C.) | 1757 | 2.17(3H.s) 2.3–2.8(3H.m) 2.8–3.0(1H.m) 3.85(3H.s) 3.91(3H.s) 4.55–4.7(1H.m) 7.1–7.45(5H,m) 7.5–7.7(1H.m) 7.96(1H.t) 8.32(1H.d) 8.88(1H.d) | 433 (M$^+$) 378 (100) | Anal Calcd for C:69.27 H:5.35 N:3.23 Found C:69.12 H:5.34 N:3.16 |

TABLE 2-continued

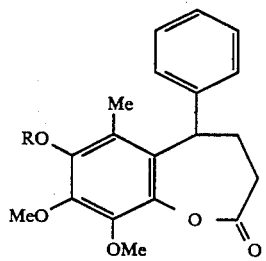

| Reference Example No. | R | Yield (%) | Property (mp) | IR spectrum (ν cm⁻¹) | NMR spectrum (δ ppm) | Mass spectrum | Elemental analysis |
|---|---|---|---|---|---|---|---|
| 5 | ⟨phenyl⟩-CO— | 74 | Colorless powder (61–63° C.) | 1736 1760 | 2.13(3H.s) 2.3–2.8(3H.m) 2.8–3.0(1H.m) 3.85(3H.s) 3.88(3H.s) 4.55–4.7(1H.m) 7.1–7.4(5H.m) 7.54(2H.t) 7.69(1H.t) 8.24(2H.d) | 432 (M+) 105 (100) High Mass Calcd. 432.1571 Found. 432.1563 | — |

| Preparation Example 1 (capsule) | |
|---|---|
| (1) Compound of Compound No. 1 | 50 mg |
| (2) Lactose | 59.5 mg |
| (3) Corn starch | 40 mg |
| (4) Light silicic anhydride | 0.5 mg |
| Total | 150 mg |

The above-mentioned components were thoroughly mixed and filled into gelatin capsules in a conventional manner.

| Preparation Example 1 (tablet) | |
|---|---|
| (1) Compound of Compound No. 1 | 50 mg |
| (2) Lactose | 48 mg |
| (3) Corn starch | 50 mg |
| (4) Polyvinylpyrrolidone | 1.5 mg |
| (5) Magnesium stearate | 0.5 mg |
| Total | 150 mg |

The above-mentioned components were mixed and tableted in a conventional manner to form tablets.

The compound according to the present invention exhibited excellent an cerebral protective activity upon oral administration, and therefore, will be useful as a pharmaceutical composition having a cerebral insufficiency improving activity. The test method and the effect are shown as follows.

Antihypoxia activity (cerebral protective activity against low oxygen under a reduced pressure)

Seven to ten ddY-strain male mice weighing 22 to 30 g were used per group. The medicine to be tested was suspended in a 1% gum arabic solution, and 50 mg/kg thereof was administered orally. Thirty minutes after administration of the drug, the mice were placed in a dessicator (volume: about one liter), followed by suction by a vacuum pump to control the pressure in the dessicator to 180 mm Hg. The time from the initiation of the pressure reduction to termination of breathing was defined as the survival time, and if the mice were alive even after elapse of 15 minutes of hypoxia loading, it was calculated as 15 minutes for comparison with the group to which the solvent was administered.

| | Results |
|---|---|
| Compound No. | Survival elongation effect (Ratio[4]) |
| 1 | 1.38* |
| 2 | 1.28* |
| 4 | 1.30* |
| 8 | 1.42* |
| 9 | 1.54* |
| 11 | 1.32* |
| 12 | 1.67* |
| 15 | 1.56* |
| 16 | 1.80* |
| 17 | 1.46* |
| Comparative Example 1[1, 3] | 1.25 |
| Comparative Example 2[2, 3] | 1.03 |

[1]Comparative Example 1: 2,3-Dimethoxy-6-(10-hydroxydecanyl)-5-methyl-1,4-benzoquinone Idebenone
[2]Comparative Example 2: 4-(3,4-Dimethoxy-6-methyl-2,5-benzoquinonyl)-1-thiomorpholino-1-oxobutane (See Japanese Unexamined Pat. Publication No. 62-226953)
[3]Dosage: 100 mg/kg
[4]Ratio of survival elongation time (min.) relative to Control (no administration)
*effective with a significant difference of P <0.05 (risk ratio 5% or less)

We claim:

1. A hydroquinonyl phenylbutyric acid amide derivative having the formula (I):

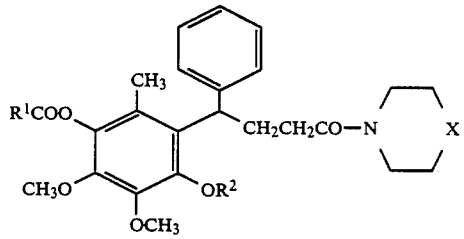

(I)

wherein R[1] represents a substituted or unsubstituted phenyl, naphthyl, pyridyl, dihydropyridyl, N-methyl-dihydropyridyl, thienyl or furyl group wherein the substituted group is selected from the group consisting of an alkyl group, hydroxyl group, alkoxy group or a halogen atom, R[2] represents a hydrogen atom, or a substituted or unsubstituted acetyl, propionyl, butyryl, benzoyl, napthoyl, furylcarbonyl, thienylcarbonyl, pyridinecarbonyl or dihydropyridinecarbonyl group wherein the substituted group is selected from the group consisting of an alkyl group, hydroxy group, alkoxy group or a halogen atom, and X represents an oxygen atom or sulfur atom pharmaceutically acceptable salt thereof.

2. A hydroquinonyl phenyl butyric acid amide derivative as claimed in claim 1, wherein, in the formula (I), $R^2$ is a hydrogen atom and $R^1$ is a phenyl group or a pyridyl group.

3. A hydroquinonylphenyl butyric acid amide derivative as claimed in claim 1, wherein in the formula (I), $R^2$ is an acetyl group of $R^1$ is a phenyl group or a pyridyl group.

4. A hydroquinonylphenyl butyric acid amide derivative as claimed in claim 1, wherein in the formula (I), $R^2$ is a benzoyl group or a nicotinoyl group and $R^1$ is a phenyl group or a pyridyl group.

5. A hydroquinonylphenyl butyric acid amide derivative, wherein said derivative is at least one compound selected from the group consisting of:
4-(3,4-dimethoxy-2-hydroxy-6-methyl-5-nicotinoyloxy)phenyl-4-phenyl-1-thiomorpholino-1-oxobutane; 4-(3,4-dimethoxy-2-hydroxy-5-isonicotinoyloxy-6-methyl)phenyl-4-phenyl-1-thiomorpholino-1-oxobutane; 4-(5-benzoyloxy-3,4-dimethoxy-2-hydroxy-6-methyl)phenyl-4-phenyl-1-thiomorpholino-1-oxobutane; 4-(5-benzoyloxy-3,4-dimethoxy-2-hydroxy-6-methyl)phenyl-4-phenyl-1-morpholino-1-oxobutane, 4-(2,5-dibenzoyloxy-3,4-dimethoxy-6-methyl)phenyl-4-phenyl-1-thiomorpholino-1-oxobutane; 4-(2-acetoxy-5-benzoyloxy-3,4-dimethoxy-6-methyl)phenyl-4-phenyl-1-thiomorpholino-1-oxobutane; and 4-(2-acetoxy-5-benzoyloxy-3,4-dimethoxy-6-methyl)-phenyl-4-phenyl-1-morpholino-1-oxobutane or a pharmaceutically acceptable salt thereof.

6. A pharmaceutical composition having a cerebral insufficiency improving activity, comprising, as an active ingredient, a pharmaceutically effective amount to improve cerebral insufficiency of a hydroquinonylphenyl butyric acid amide derivative having the formula (I):

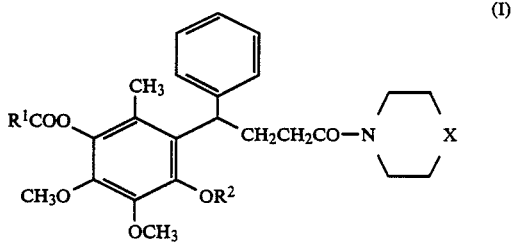

wherein $R^1$ represents a substituted or unsubstituted phenyl, naphthyl, pyridyl, dihydropyridyl, N-methyldihydropyridyl, thienyl or furyl group wherein the substituted group is selected from the group consisting of an alkyl group, hydroxyl group, alkoxy group or a halogen atom, $R^2$ represents a hydrogen atom, or a substituted or unsubstituted acetyl, propionyl, butyryl, benzoyl, naphthoyl, furylcarbonyl, thienylcarbonyl, pyridinecarbonyl or dihdropyridinecarbonyl group wherein the substituted group is selected from the group consisting of an alkyl group, hydroxy group, alkoxy group or a halogen atom, and X represents an oxygen atom or a sulfur atom or a pharmaceutically acceptable salt thereof, and a pharmaceutically acceptable carrier therefor.

* * * * *